US009943232B2

(12) United States Patent
Kroetz et al.

(10) Patent No.: US 9,943,232 B2
(45) Date of Patent: Apr. 17, 2018

(54) THERMOMETRY HEATING AND SENSING ASSEMBLY

(71) Applicant: Welch Allyn, Inc., Skaneateles Falls, NY (US)

(72) Inventors: John P. Kroetz, Pittsford, NY (US); John A. Lane, Weedsport, NY (US); David E. Quinn, Auburn, NY (US); John T. Delaney, Auburn, NY (US); Matthew D. Mulin, Memphis, NY (US); Matthew J. Kinsley, Marcellus, NY (US); Steven R. Slawson, Camillus, NY (US); Scott A. Martin, Warners, NY (US); David M. Antos, Constantia, NY (US); Ray D. Stone, Camilus, NY (US); William N. Cuipylo, Auburn, NY (US); Adam P. Vallee, Cato, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 265 days.

(21) Appl. No.: 14/612,886

(22) Filed: Feb. 3, 2015

(65) Prior Publication Data
US 2015/0216421 A1    Aug. 6, 2015

Related U.S. Application Data

(60) Provisional application No. 61/935,106, filed on Feb. 3, 2014.

(51) Int. Cl.
*A61B 5/00* (2006.01)
*A61B 5/01* (2006.01)
(Continued)

(52) U.S. Cl.
CPC .................. *A61B 5/01* (2013.01); *G01K 1/18* (2013.01); *G01K 13/002* (2013.01);
(Continued)

(58) Field of Classification Search
CPC ......... A61B 5/01; A61B 5/015; G01K 13/002
(Continued)

(56) References Cited

U.S. PATENT DOCUMENTS

| 4,987,579 A | 1/1991 | Yoshinaka et al. |
| 5,116,136 A | 5/1992 | Newman et al. |

(Continued)

FOREIGN PATENT DOCUMENTS

| EP | 417274 A1 | 3/1991 |
| EP | 979394 B1 | 10/2001 |

(Continued)

OTHER PUBLICATIONS

Millonig, "Assessing and Managing Fever", University of Minnesota College of Pharmacy, Center for Leading Healthcare Change, Publication date: Nov. 9, 2012 (7 pages).
(Continued)

*Primary Examiner* — Daniel Cerioni

(57) ABSTRACT

A thermometry apparatus includes a distal probe tip having a hollow interior. An insulating support is at least partially disposed within the interior of the distal probe tip. The insulating support is configured to receive at least one of at least one heating element and at least one temperature sensing element. According to one version, the insulating support is a flexible circuit strip configured to receive the at least one heating element(s) to protect the leads from damage and premature breakage.

12 Claims, 8 Drawing Sheets

(51) Int. Cl.
*G01K 1/18* (2006.01)
*G01K 13/00* (2006.01)

(52) U.S. Cl.
CPC ... *A61B 2562/0271* (2013.01); *A61B 2562/12* (2013.01); *A61B 2562/164* (2013.01); *Y10T 29/49124* (2015.01)

(58) Field of Classification Search
USPC .......................................................... 600/549
See application file for complete search history.

(56) References Cited

U.S. PATENT DOCUMENTS

| | | | |
|---|---|---|---|
| 5,178,468 | A | 1/1993 | Shiokawa et al. |
| 5,406,053 | A * | 4/1995 | Masreliez ............ B23K 3/0315 |
| | | | 219/229 |
| 5,581,238 | A | 12/1996 | Chang et al. |
| 5,632,555 | A | 5/1997 | Gregory et al. |
| 5,792,070 | A | 8/1998 | Kauphusman et al. |
| 6,280,397 | B1 | 8/2001 | Yarden et al. |
| 6,511,478 | B1 | 1/2003 | Burnside et al. |
| 6,547,745 | B1 | 4/2003 | Rubinstein |
| 6,827,487 | B2 | 12/2004 | Baumbach |
| 6,839,651 | B2 | 1/2005 | Lantz et al. |
| 6,866,391 | B2 | 3/2005 | Krausse |
| 6,886,978 | B2 | 5/2005 | Tokita et al. |
| 6,890,096 | B2 | 5/2005 | Tokita et al. |
| 6,976,783 | B2 | 12/2005 | Chen |
| 7,059,767 | B2 | 6/2006 | Tokita et al. |
| 7,284,904 | B2 | 10/2007 | Tokita et al. |
| 7,293,915 | B2 | 11/2007 | Chen |
| 7,299,148 | B2 | 11/2007 | Hunt et al. |
| 7,314,310 | B2 | 1/2008 | Medero |
| 7,316,507 | B2 | 1/2008 | Sisk et al. |
| 7,374,336 | B2 | 5/2008 | Fraden |
| 7,484,887 | B2 | 2/2009 | Shidemantle et al. |
| 7,494,274 | B2 | 2/2009 | Sisk et al. |
| 7,507,021 | B2 | 3/2009 | Yerlikaya et al. |
| 2002/0123690 | A1 | 9/2002 | Fraden |
| 2003/0023398 | A1 | 1/2003 | Lantz et al. |
| 2004/0076215 | A1 | 4/2004 | Baumbach |
| 2004/0254497 | A1 | 12/2004 | Fraden et al. |
| 2005/0220170 | A1 | 10/2005 | Tokita et al. |
| 2006/0106365 | A1 * | 5/2006 | Lane ...................... G01K 1/083 |
| | | | 604/508 |
| 2007/0055171 | A1 | 3/2007 | Fraden |
| 2007/0100253 | A1 | 5/2007 | Sisk et al. |
| 2008/0019415 | A1 | 1/2008 | Kraus |
| 2008/0089387 | A1 | 4/2008 | Price |
| 2009/0135884 | A1 | 5/2009 | Sisk et al. |
| 2009/0141771 | A1 | 6/2009 | Owen et al. |
| 2009/0168838 | A1 | 7/2009 | Harr et al. |
| 2009/0285260 | A1 | 11/2009 | Stone et al. |
| 2011/0137201 | A1 | 6/2011 | Fraden |
| 2011/0249701 | A1 | 10/2011 | Bieberich et al. |
| 2011/0265320 | A1 | 11/2011 | Sisk et al. |
| 2012/0024833 | A1 | 2/2012 | Klewer et al. |
| 2015/0036719 | A1 * | 2/2015 | Koduri ................. G01K 13/002 |
| | | | 374/152 |

FOREIGN PATENT DOCUMENTS

| | | |
|---|---|---|
| EP | 1249691 A1 | 10/2002 |
| EP | 1299044 B1 | 6/2005 |
| EP | 1643228 A1 | 4/2006 |
| EP | 1645236 A1 | 4/2006 |
| EP | 1783469 A1 | 5/2007 |
| EP | 1783470 A2 | 5/2007 |
| EP | 1909086 A2 | 4/2008 |
| EP | 2075559 A2 | 7/2009 |
| EP | 2161556 A1 | 3/2010 |
| GB | 2395794 A | 6/2004 |
| WO | 2001/027580 A1 | 4/2001 |
| WO | 2002/000129 A1 | 1/2002 |
| WO | 2003/002965 A1 | 1/2003 |
| WO | 2005/048809 A1 | 6/2005 |
| WO | 2006/010108 A2 | 1/2006 |
| WO | 2008/139347 A1 | 11/2008 |
| WO | 2010/014354 A1 | 2/2010 |

OTHER PUBLICATIONS

Watlow® Thermal Solutions for Medical and Clinical Applications, 2012 Watlow Electric Manufacturing Company, Publication date: 2012 (20 pages).

Yin et al., "Microstructure, Property and Processing of Functional Ceramics", Metallurgical Industry Press, Springer Berlin Heidelberg, 2010 (Abstract).

* cited by examiner

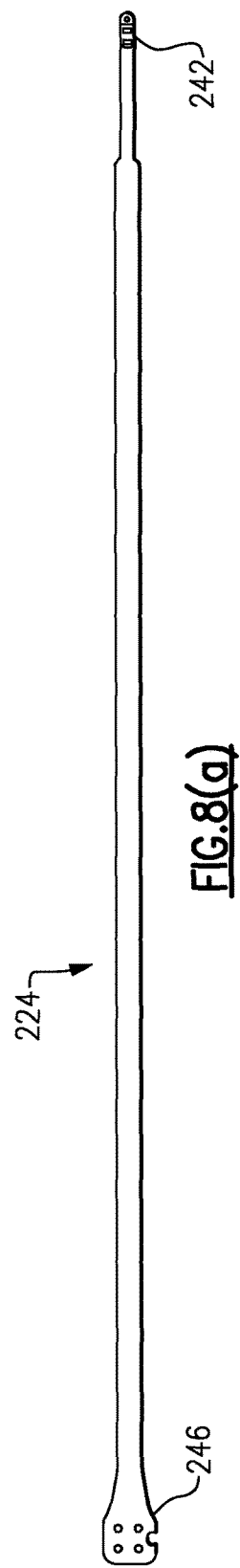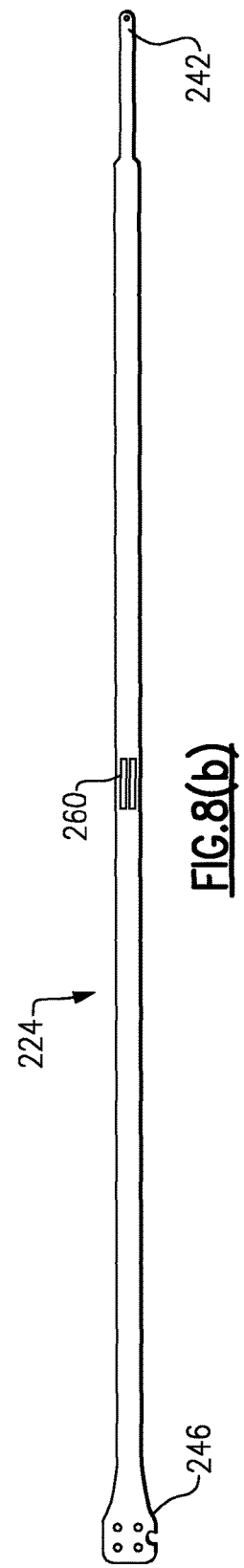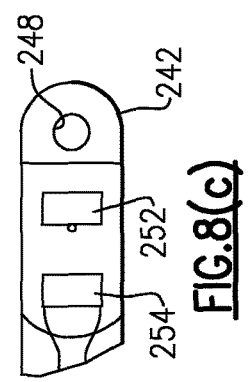

THERMOMETRY HEATING AND SENSING ASSEMBLY

CROSS REFERENCE TO RELATED APPLICATION

This application claims priority under relevant portions of 35 U.S.C. § 119 to U.S. Patent Application Ser. No. 61/935,106, filed Feb. 3, 2014, and entitled: Thermometry Heating and Sensing Assembly, the entire contents of this document being incorporated by reference.

TECHNICAL FIELD

This application is generally directed to the field of medical devices and more specifically to a patient thermometry heating and sensing assembly, including an improved thermometry probe tip design.

BACKGROUND

Medical diagnostic apparatus, such as the SureTemp® thermometer manufactured and sold by Welch Allyn of Skaneateles Falls, N.Y., are known for measuring the body temperature of a patient. A probe includes a proximal end that is connected by means of a tethering cord to a device housing, the latter containing a processor and a display. The probe is defined by an elongate probe body, including a conically shaped distal probe tip that is configured to retain a temperature sensor or sensing element, as well as a heating element. The heating element is used in order to preheat the probe given the temperature differences between the environment and the core body temperature of a patient at an intended target (e.g., the axilla, rectum, sublingual pocket), so as to effectively shorten the amount of time that is required to take a temperature measurement.

A probe 14 of a prior art thermometry apparatus 10 is illustrated in FIGS. 1 and 2. As noted, the probe 14 includes a distal probe tip 18, the latter being defined by a substantially conical shape including a hollow interior. The heating element, such as an electrical resistor 24, is secured by epoxy along one circumferential portion of an interior wall 20 of the distal probe tip 18 and the temperature sensing element, such as a thermistor 28, is also attached using an epoxy or suitable adhesive along another circumferential portion of the interior wall 20, each of the heating element and temperature sensing element being adjacent to the distal end 19 of the distal probe tip 18. Sets of electrical leads 32, 34, in the form of low gauge copper wires, extend proximally from each of the resistor 24 and thermistor 28, respectively, and further extend through the body of the probe 14 to a connector on the proximal end (not shown) of the probe 14 for attachment to the device housing (not shown). The electrical leads 32, 34 provide electrical power to the retained components 24, 28 and also permit the transmission of signals from the temperature sensing element to the attached device housing (not shown) for processing and display, such as in the course of a typical patient examination.

As shown more clearly in FIG. 2 and during the normal course of use of this thermometry apparatus 100, the electrical leads 32, 34 extend away from the interior wall mounted components 24, 28 with little additional support, especially at the mounted ends of the leads 32, 34, and are therefore susceptible to breakage. Premature breakage of the electrical leads 32, 34 frequently requires a complete replacement of the entire thermometry probe 14, and not just the interior components.

Based in part on the foregoing, there is a general and ongoing need to improve the durability and manufacturability of thermometry assemblies, so as to improve their reliability and increase working life.

Because the temperature sensing element and the heating element are eccentrically mounted to the interior wall of the probe tip, there may also be inconsistencies in terms of heat generation and detection. As a result, there is another general need to improve these characteristics in a thermometry apparatus.

BRIEF DESCRIPTION

According to one aspect, there is provided a temperature measuring apparatus comprising a distal probe tip having an interior and an inner wall. A temperature sensing element is attached to the inner wall. At least one heating element is attached to the inner wall of the housing, the heating element being further connected to a flexible circuit strip.

In one version, the thermometry apparatus can include a shaped mandrel which is initially disposed within the probe tip, the mandrel including at least one feature for securing to the flexible circuit strip during the assembly process. According to one version, the flexible circuit strip includes an opening at a distal end and the mandrel includes a protrusion that is sized to engage the distal opening. In this version, the mandrel is removed from the apparatus prior to final manufacture and test.

In accordance with another aspect, there is described a thermometry apparatus comprising a distal probe tip having a hollow interior. An insulating support is fixedly secured within the interior of the distal probe tip and a temperature sensing element is attached to the insulating support.

In at least one version, the apparatus further comprises at least one heating element that is disposed with the hollow interior of the tip. The at least one heating element can be attached to the insulating support or to a flexible circuit strip.

According to at least one embodiment, a ceramic disc or other suitably shaped planar member is used as the insulating support in which the at least one heater element can be disposed on an outer periphery of one side of the support. According to one preferred version, a pair of heater elements can be disposed on diametrically opposed portions along the outer periphery of the insulating support on a first side thereof. In another version, a heating element can be eliminated entirely from the tip assembly with a temperature sensing element being attached to one side of the support. In at least one embodiment, the heater elements are electrical resistors and the temperature sensing element is a thermistor. In one version, the temperature sensing element can be disposed adjacent the center of the support on a parallel and opposed second surface of the insulating support.

In at least one version, at least one or each of the heating element(s) and the temperature sensing element can be thin-film printed onto respective surfaces of the insulating support.

In accordance with another aspect, there is provided a method for configuring a probe tip to measure temperature, the method comprising the steps of providing an insulating support, fixedly disposing the insulating support within a hollow interior of the probe tip, and securing a temperature sensing element within the interior of the probe tip. In another version, at least one heating element can be further provided. In accordance with the method, the at least one heating element and the temperature sensing element are attached to opposite surface of the insulating support. In another version, the at least one heating element can be attached to a flexible circuit strip.

Preferably, the support is made from an insulating material and according to at least one embodiment is made from a ceramic. In at least one embodiment, the insulating support includes an outer periphery that substantially matches that of the inner wall of the probe tip in which the substrate can be secured using an interference or press fit. In one such embodiment, the support can be formed as a disc. According to another version, the insulating support need only match a portion of the internal surface of the probe tip and be fixedly attached therein.

According to at least one embodiment, the at least one heating element and the temperature sensing element can be attached to opposing parallel surfaces of the insulating support. In at least one version, at least one or each of the temperature sensing element and the at least one heating element are substrates that are attached to the insulating support by means of thin-film printing. In another version, only the temperature sensing element is attached to the insulating support and heating elements are entirely eliminated from the tip assembly.

In at least one version, a pair of heating elements are disposed along an outer periphery of the insulating support on one side or surface thereof, the pair of heating elements being substantially diametrically opposed and the temperature sensing element being attached at substantially the center of the opposing side or surface of the insulative support. As a result, even circumferential heat generation and heat detection can be advantageously provided.

According to yet another aspect, there is provided a thermometry apparatus comprising a distal probe tip having a hollow interior, and a temperature sensing element disposed within the hollow interior. An insulating support is at least partially mounted within the interior of the distal probe tip; and at least one of the temperature sensing element and the heating element being attached to the support.

According to yet another aspect, there is provided a method of manufacturing a thermometry apparatus in which a thermometry probe is provided, including a distal probe tip made from a thermally conductive material and in which the probe tip has a hollow interior and an interior wall. A temperature sensing element is attached to the interior wall and a heating element is provided as well as a flexible circuit strip having a distal end that is configured to retain the heating element. The heating element is attached to the flexible circuit strip; and the heating element is attached to the interior wall of the tip.

One advantage that is provided by the herein described thermometry apparatus is that of a simpler manufacture in which the insulating support can commonly retains at least one or each of the heating element(s) and temperature sensing element. The foregoing arrangement significantly saves costs in terms of labor and manufacture.

Another advantage provided is that of improved reliability and working life of a thermometry probe, wherein the electrical leads to the temperature sensing element and the heating element(s) are less susceptible to premature breakage.

Yet another advantage is that the disposition of circumferentially disposed heating elements on the insulating support provides uniformity in terms of overall heat generation for the thermometry apparatus, as well as heat detection.

These and other features and advantages will be readily apparent from the following Detailed Description, which should be read in conjunction with the accompanying drawings.

BRIEF DESCRIPTION OF THE DRAWINGS

FIG. 8(a) depicts one side of a flexible circuit strip for use in a thermometry apparatus, such as the apparatus shown in FIG. 7;

FIG. 8(b) depicts the opposite side of the flexible circuit strip depicted in FIG. 8(a); and FIG. 8(c) is an enlarged view of the distal end of the flexible circuit strip of FIGS. 8(a)-8(b).

DETAILED DESCRIPTION

The following description generally relates to a medical thermometry apparatus and more specifically to embodiments of a distal probe tip that retains at least one heating element and a temperature sensor. It will be readily apparent that other variations and modifications are possible. In addition, certain terms are used throughout this discussion to provide a suitable frame of reference in regard to the accompanying drawings. These terms, which include "upper", "lower", "inner", "outer", "distal", "proximal" and the like are not intended to limit the scope of the inventive concepts, unless specified otherwise.

The drawings are also intended to clearly detail the salient features of the invention. In that regard, the drawings are not necessarily drawn to scale and the reader should not otherwise rely upon the drawings.

Figure 1:
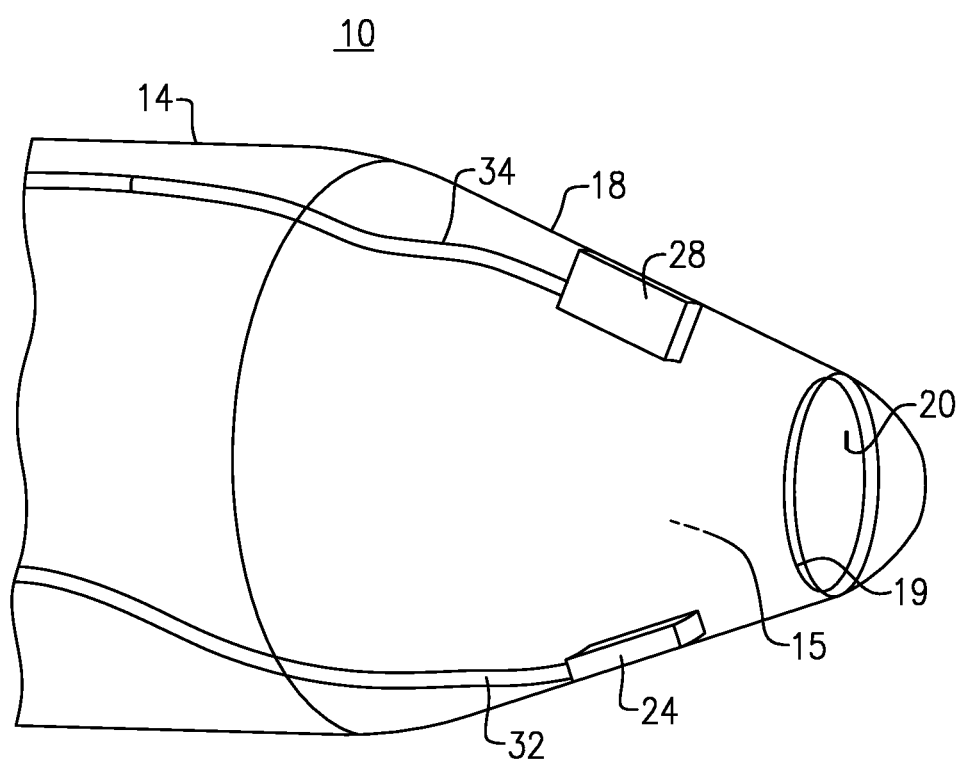
FIG. 1 is a partial sectioned view of a probe tip for a thermometry apparatus in accordance with the prior art.
Figure 2:
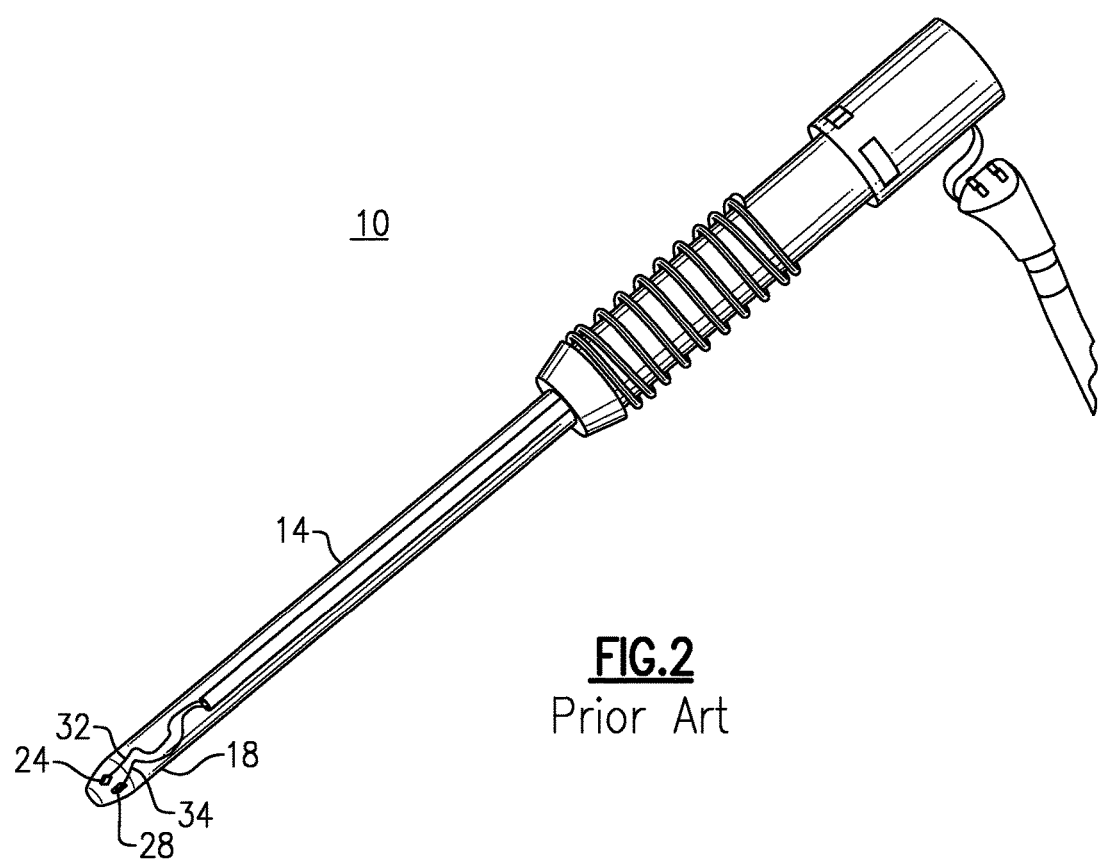
FIG. 2 is a perspective view of a probe for a thermometry apparatus including the probe tip of FIG. 1.
Figure 3:
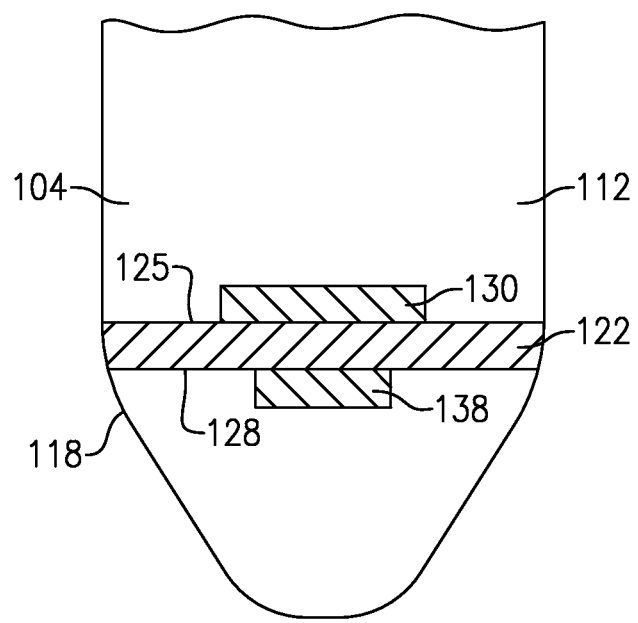
FIG. 3 is a partial sectioned view of a thermometry probe tip which is made in accordance with an exemplary embodiment.

Referring to FIG. 3, a sectioned partial view of a probe tip 104 in accordance with an exemplary embodiment is shown, and more specifically a distal end 118 thereof. The distal end 118 of the probe tip 104 is part of a thermometry apparatus 100, similar to that previously described as part of a temperature probe and having features shown in FIG. 2, the tip 104 being tethered to an apparatus housing (not shown), which includes various components, including a processor and signal conditioning electronics. The probe tip 104 according to this exemplary embodiment is defined by a substantially conical configuration having a hollow interior 112 as well as a probe shaft (not shown) extending proximally from the probe tip 104. The probe tip 104 is sized and configured for placement relative to a target of interest, such as the axillary region, under the tongue, the rectum or other suitable area of the patient's body (not shown) from which temperature can be reliably measured. The temperature probe, including the probe tip 104 and the extending probe shaft, can be manufactured from a stainless steel or from another suitable material possessing a high thermal conductivity.

As shown and in lieu of mounting the various heat generating and detecting components against portions of the interior wall of the probe tip 104, a support 122 made from a ceramic or other suitable electrically insulating material is fitted within the tip interior 112. Moreover and in accordance with this specific embodiment, the insulating support 122 is defined by a planar disk having an inner surface 125 and an opposing outer surface 128 in which the insulating support 122 is sized to create a press fit or an interference fit, as installed within the hollow interior 112 of the probe tip 104. Alternatively, the support 122 can assume other shapes, as discussed herein, in which the insulating support 122 is not necessarily required to assume the precise geometry of the internal surface of the probe tip 104, provided that the support can be securely attached within the confines of the probe tip 104 and is preferably planar in terms of its construction.

Still referring to FIG. 3 and according to this exemplary embodiment, at least one heating element 130, such as an electrical resistor, is attached to the inner surface 125 of the insulating support 122 and a temperature sensing element 138 is attached to the outer surface 128 of the insulating support 122. The temperature sensing element 138 can be, for example, a thermistor or a thermocouple. When mounted and as shown, the outer surface 128 of the mounted insulating support 122 faces the distal end 118 of the probe tip 104 and the opposing inner surface 125 of the support 122 faces the proximal end of the probe. In general, mounting at least one of the above elements 130, 138 to a fixed component, in this instance the insulating support 122, provides advantages in terms of heating and manufacturability of the probe tip 104. In addition, the electrical leads (not shown) of the attached components 130, 138 can be more reliably secured within the probe tip 104 and therefore much less prone to premature breakage. Alternatively, the heating element 130 can be removed entirely with only the temperature sensing element 138 being attached to the insulating support 122.

Figure 4:
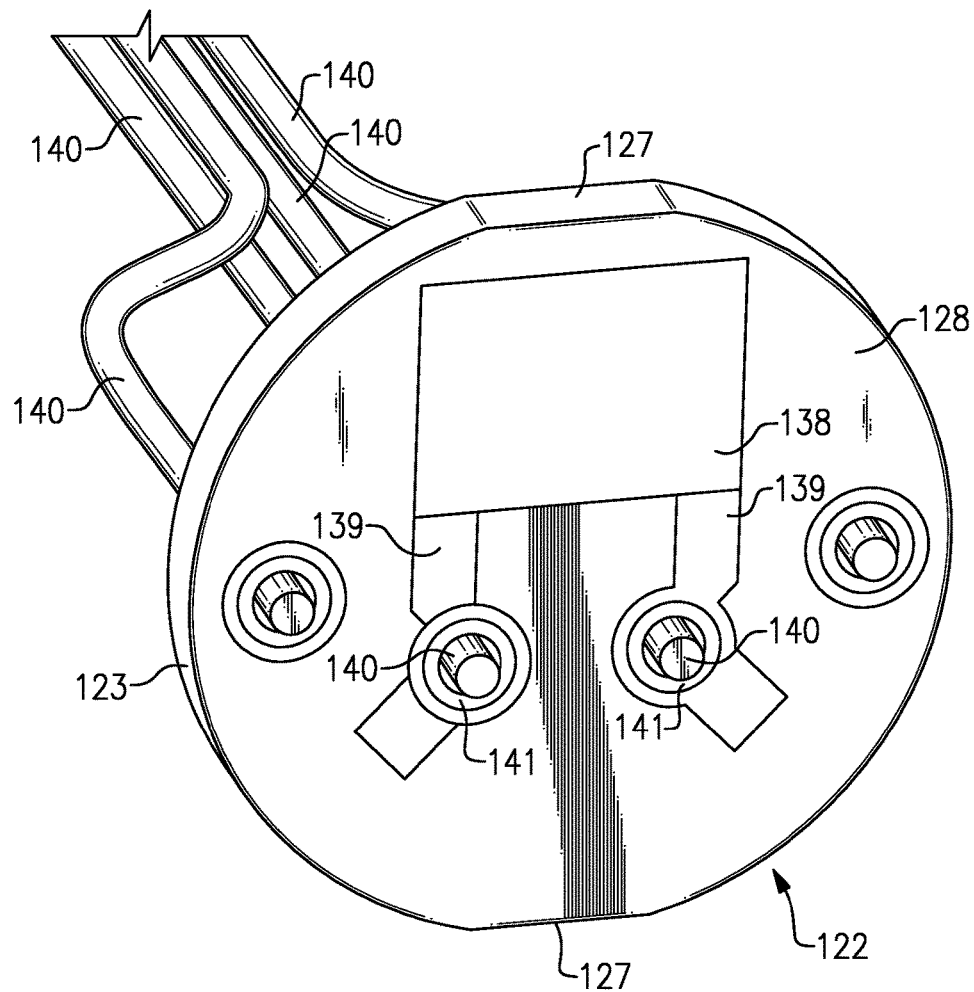
FIG. 4 is a perspective view of a portion of an exemplary substrate for use in the probe tip of FIG. 3.
Figure 5:
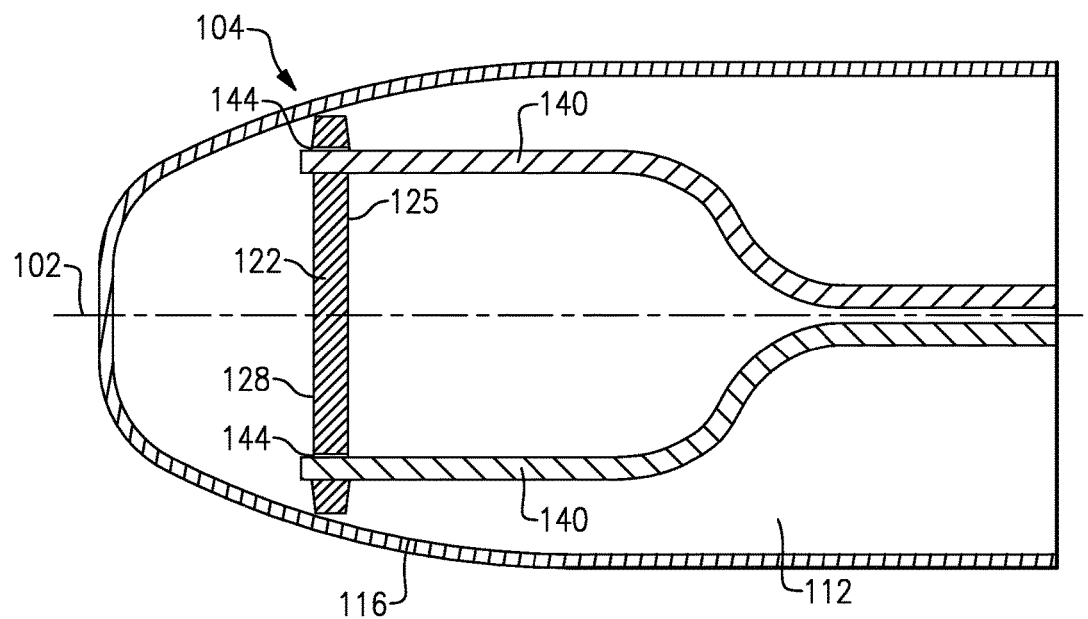
FIG. 5 is a sectioned side elevational view of a probe tip made in accordance with an exemplary embodiment.
Figure 6:
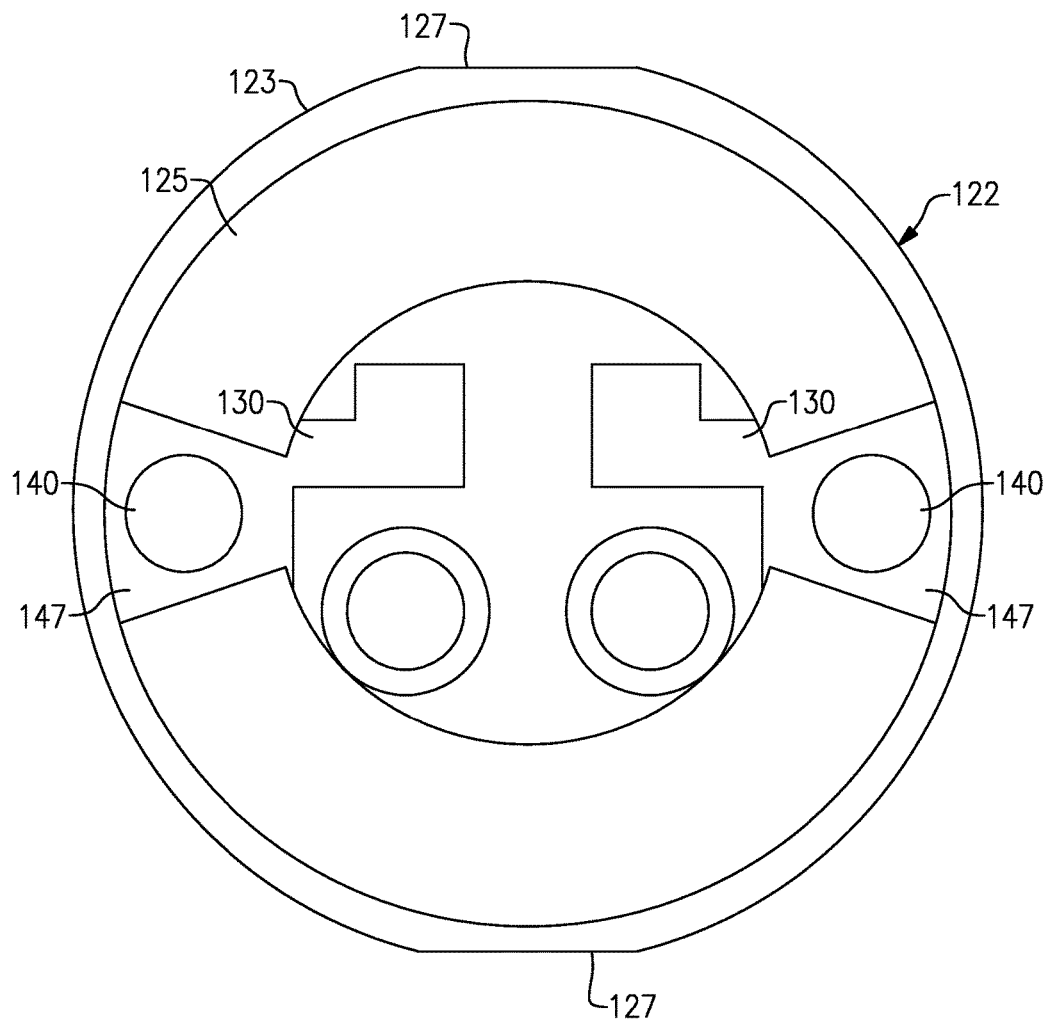
FIG. 6 is a bottom facing view of an exemplary substrate for use in a temperature sensing and heating apparatus.

Reference is now made to a more specific exemplary embodiment, as depicted in FIGS. 4-6. Similar parts are herein labeled with the same reference numerals for the sake of clarity. According to this embodiment, a distal tip 104 of a thermometry apparatus 100 includes a hollow interior 112 that is sized to receive an insulating support 122 made from a ceramic or other suitable material. The insulating support 122, according to this specific embodiment, is defined by a disc-like configuration including an inner surface 125 and an opposing outer surface 128, as well as an outer periphery 123 that is substantially circular with the exception of two flattened portions 127 that are diametrically opposed to one another. In this version, the flattened portions 127 facilitate a fit within the interior of the distal tip 104 with the inner surface 125 facing the proximal end of the probe and the outer surface 128 facing the distal end 118 of the tip 104.

As shown in FIG. 6 and according to this exemplary embodiment, a pair of heating elements 130, such as electrical resistors, are secured to the inner surface 125 of the insulating support 122 at substantially diametrically opposed portions (i.e., approximately 180 degrees apart) that are adjacent the outer periphery 123 of the support 122. According to this specific version, the heating elements 130 are each thin-film, thereby providing a substrate which can be printed onto the inner surface 125 of the support 122. Alternatively, a resistor or other heating element (not shown) could be mounted using epoxy, adhesive or other suitable securing means. A corresponding set of electrical leads 140 each include distal ends 141 that are received within respective openings 144 provided in the insulating support 122. Each opening 144 includes a bordering electrically conductive area 147 configured to provide electrical power to each of the resistive (heating) elements 130, as attached to the insulating support 122 as shown more clearly in FIGS. 4-6. The leads 140 are fixedly mounted to the formed openings 144 and placed into electrical contact with the disposed heater elements 130 via the conductive areas 147.

As shown in FIG. 4, at least one temperature sensing element 138, such as a thermistor or thermocouple, is mounted to the outer facing surface 128 of the support 122 according to this embodiment. According to the exemplary embodiment and like the heating elements 130, the temperature sensing element 138 can be a thin-film, which is printed onto the outer surface 128 of the insulating support 122. Alternatively, however, other securing means such as an epoxy or suitable adhesive can also be utilized. The at least one temperature sensing element 138 can be mounted anywhere along the outer surface 128. According to this exemplary embodiment, a single temperature sensing element 138 is thin-film printed at about the center of the outer surface 128 and in which a set of electrical leads 140 engage extending conductive portions 139 of the temperature sensing element 138 through a pair of spaced openings 144 provided in the insulating support 122.

As to manufacture and referring to FIGS. 4-6, the insulating support 122 can be securely attached within the hollow interior 112 of the probe tip 104. For example, assembly aids, such as grooves or stops, can be provided in the inner wall 116 of the probe tip 104 to assist in the positioning of the insulating support 122, which is positioned substantially transverse to the center axis 102, FIG. 5, of the probe tip 104. According to one version, not shown, a set of spaced portions (not shown) can be provided on the inner surface of the probe tip 104. Preferably, the temperature sensing element 138 and the heating elements 130 can be secured as substrates using thin-film printing or other suitable means prior to assembly of the insulating support 122 within the interior 112 of the probe tip 104, and wherein each of the distal ends 141 of the electrical leads 140 can be secured within the openings 144 of the insulating support 122. Alternatively and as previously discussed, the heating elements 130 can be eliminated entirely from the foregoing assembly with the temperature sensing element 138 being secured to the insulating support 122.

In operation, the thermometry apparatus 100 is energized in a known manner such as through a switch provided on the exterior of the device housing (not shown), enabling electrical power to be applied to each of the heating elements 130 and the temperature sensing element 138 as the probe tip 104 is brought into substantial proximity with a target of interest (e.g., the axillary area) of a subject (not shown). As previously noted, the probe tip 104 is preheated due to the substantial difference between average body core temperature (98 degrees F.) and that of ambient conditions (65-80 degrees F.) by the application of electrical power (current) to each of the circumferentially disposed heating elements 130 according to this exemplary embodiment. The peripheral and circumferential positioning of the conductive areas 147 of the heating elements 130 at the outer periphery 123 of the insulating support 122 provides uniformity in heat generation of the insulating support 122 to the probe tip 104 and relative to the nominal temperature of the body (not shown) of the subject, this temperature being uniformly detected by the temperature sensing element 138. Alternatively and in the absence of heating elements, the foregoing pre-heating step would not be required. Following the above-noted pre-heating step, temperature determinations of the target can be made using the contained temperature sensing element 138 wherein the signals, indicative of a change in temperature (e.g., current) are transmitted along the electrical leads 140 to a processor (not shown) of the thermometry apparatus 100. The processor can be powered by batteries or other source and is further configured to control the operation of the heating elements and conductive areas. Advantageously and due to the placement of the above components as described, the herein described probe tip design is also more reliable in terms of performance as compared to known thermometry apparatus. That is and at a minimum, heat generation and heat detection is more efficient, uniform and repeatable.

In addition to providing uniformity in terms of heat generation and heat detection, the herein described placements of at least one of the heating and temperature sensing elements 130, 138 to a single component, such as the insulating support 122, provides improved stability for each of the mounted electrical leads 140.

Figure 7:
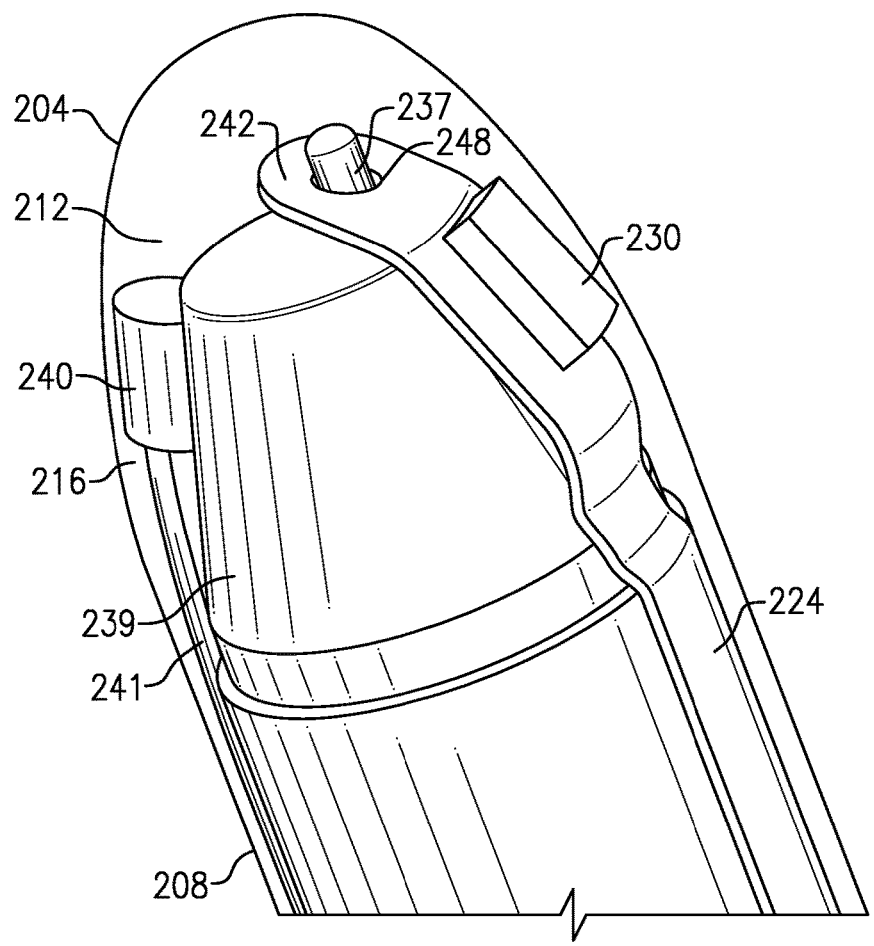
FIG. 7 is a sectioned perspective view of a probe tip of a thermometry apparatus in accordance with another exemplary embodiment.

With reference to FIG. 7, another exemplary embodiment of a thermometry apparatus 200 includes an elongate probe body 208 having a substantially conical probe tip 204 that is fabricated from a metallic or other thermally conductive material, such as stainless steel. The probe tip 204 is defined by a hollow interior 212 having an interior circumferential wall 216. The probe body 208 is only partially shown in this view, wherein the remainder of the probe body and thermometry apparatus 200 is similar to that depicted in FIG. 2 in which the proximal end of the probe is electrically and mechanically connected by a tether to a housing (not shown) containing a processor, a power source and a display.

According to this specific embodiment, a flexible circuit strip 224 having a set of embedded leads is attached to the heating element 230 and provides an electrical attachment point for the heating element 230. The heating element 230 is attached directly to the interior circumferential wall 216 of the distal probe tip 204, which allows for the most efficient transfer of heat to the wall 116. More specifically, the flexible circuit strip 224 is sized to extend over the length of the probe body and to the proximal end thereof. As shown, the flexible circuit strip 224 is secured at a distal end 242 to a radial protrusion 237 of a conical mandrel 239, the latter being initially placed within the hollow interior 212 of the distal probe tip 104 during an assembly operation. A temperature sensing element 240, such as a thermistor, is further disposed on an opposing side of the interior circumferential wall 216 of the probe tip 204.

An exemplary flexible circuit strip 224 is shown in FIGS. 8(a)-8(c). According to this version, the flexible circuit strip 224 is defined by a flat elongate member made from an insulative material, such as polyimide, and having a set of embedded leads formed in a multi-layered structure. The proximal end 246 of the strip 240 includes at least one connective feature for mechanical and electrical attachment to a proximal end connector of the probe (not shown), in which the latter is attached to a device housing (not shown) in a manner similar to that shown in FIG. 2. As shown in FIGS. 8(a) and 8(c), the distal end 242 of the flexible circuit strip 224 includes the attachment surface(s) for the heating element 230. According to this exemplary embodiment, a pair of attachment pads 252, 254 are provided in spaced relation to a distal end opening 248, the latter being sized for reception by the mandrel protrusion 237.

During an exemplary assembly process, the heating element 230 is applied to the flexible circuit strip 240 and more specifically the leads of the heating element are directly soldered to the attachment pads 252, 254. The temperature sensing element 240, as well as the flexible circuit strip 224 and attached heating element 230 are then loaded onto the assembly mandrel 239 with the flexible circuit strip 224 being attached to the extending protrusion 237 of the mandrel 239 through the distal opening 248 of the flexible circuit strip 224. A suitable adhesive is applied to the outward facing surfaces of the temperature sensing element 240 and the heating element 230. The conical probe tip 204 is then slid onto the mandrel 239 and the heating element 230 and the temperature sensing element 240 are adhered to the interior circumferential wall 218 of the probe tip 204, such as shown in FIG. 7. Once the adhesive is cured, the mandrel 239 can be removed from the interior of the probe tip 204 and discarded. The extending leads 241 of the temperature sensing element 240 can be attached (soldered) to intermediate attachment pads formed 260 on the flexible circuit strip 224, according to this exemplary embodiment.

In operation, the thermometry apparatus 200 according to this specific embodiment can be energized using a switch or other actuable element on the housing (not shown), which creates the preheating of the probe tip upon the application of electrical power to the heating element 230 from the contained power source (e.g., batteries). Because the electrical leads are embedded within the circuit strip 224, the leads are not subject to premature breakage. The probe tip 204 is pre-heated wherein the temperature changes induced due to the intended target can be detected by the temperature sensing element 240, with the resulting signals being transmitted via the flexible circuit strip 224 to the processor (not shown) of the thermometry apparatus 200.

PARTS LIST FOR FIGS. 1-8(c)

10 thermometry apparatus
14 temperature probe
15 hollow interior
18 distal probe tip
19 distal end
20 interior wall
24 heating element
28 temperature sensing element
32 electrical leads
34 electrical leads
100 thermometry apparatus
102 center axis, probe
104 probe tip
112 interior, hollow
116 inner wall
118 distal end, probe tip
122 insulating support
123 outer periphery, support
125 inner surface, support
127 flattened areas, support
128 outer surface, support
130 heating elements
138 temperature sensing element
139 conductive portions, temperature sensing element
140 electrical leads
141 distal ends, electrical leads
144 openings, spaced
147 conductive areas
200 thermometry apparatus
204 probe tip 208 probe body
212 distal end
216 interior circumferential wall
224 flexible circuit board
230 heating element
237 protrusion, distal
239 mandrel, assembly
240 temperature sensing element
241 leads, temperature sensing element
242 distal end, flexible circuit board
246 proximal end, flexible circuit board
248 distal opening, flexible circuit board
252 resistor pad
254 resistor pad
260 pads, attachment intermediate It will be readily apparent that other variations and modifications are possible in addition to those described in accordance with the inventive concepts of this application and in accordance with the following claims.

We claim:

1. A thermometry apparatus comprising:
    a thermometry probe including a distal probe tip made from a thermally conductive material, the distal probe tip having a tip housing defined by a hollow interior, the tip housing having an exterior surface and an opposing interior surface;
    a heating element;
    a temperature sensing element attached to the interior surface of the tip housing; and
    a flexible circuit strip having a distal end retaining the heating element, the heating element being attached to the interior surface of the tip housing and in which the flexible circuit strip is an elongate member made from an electrically insulative material having imbedded leads, the flexible circuit strip further having a proximal end extending to a proximal end of the probe and a distal opening sized for receiving a protrusion of an assembly mandrel disposed in the tip housing, the assembly mandrel being positioned within the hollow interior to retain and initially position the flexible circuit strip, heating element and temperature sensing element relative to the interior surface of the tip housing and wherein the assembly mandrel is removable after the flexible circuit strip, heating element and temperature sensing element are secured within the tip housing.

2. The thermometry apparatus of claim 1, wherein the heating element and the temperature sensing element are disposed on opposing sides of the interior surface of the tip housing.

3. The thermometry apparatus of claim 1, in which the distal probe tip and the assembly mandrel are conical.

4. The thermometry apparatus of claim 1, in which the proximal end of the flexible circuit strip is configured for mechanical and electrical attachment to a proximal end connector of the probe.

5. The thermometry apparatus as recited in claim 1, in which the temperature sensing element is at least one of a thermistor and a thermocouple.

6. The thermometry apparatus of claim 1, in which the distal end of the flexible circuit strip includes an attachment surface for the heating element.

7. The thermometry apparatus of claim 1, wherein the flexible circuit strip includes a pair of attachment pads provided in spaced relation to the distal opening.

8. The thermometry apparatus of claim 7, in which leads of the heating element are soldered to the attachment pads.

9. The thermometry apparatus of claim 1, wherein the flexible circuit strip includes intermediate attachment pads and in which extending leads of the temperature sensing element are soldered to the intermediate attachment pads.

10. The thermometry apparatus of claim 1, in which the flexible circuit strip is made from polyimide.

11. The thermometry apparatus of claim 4, in which the proximal end of the flexible circuit strip includes a connective feature for mechanical and electrical attachment to a proximal end connector of the thermometry probe.

12. The thermometry apparatus of claim 1, in which the flexible circuit strip, including the imbedded leads, is defined by a multi-layered structure.

* * * * *